(12) United States Patent
Italiaie et al.

(10) Patent No.: US 10,543,022 B2
(45) Date of Patent: Jan. 28, 2020

(54) SPINAL IMPLANT SYSTEM AND METHOD

(71) Applicant: Warsaw Orthopedic, Inc, Warsaw, IN (US)

(72) Inventors: Christel Italiaie, Memphis, TN (US); Larry Thomas McBride, Jr., Memphis, TN (US); Mark R. Grizzard, Munford, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 15/290,866

(22) Filed: Oct. 11, 2016

(65) Prior Publication Data

US 2018/0098798 A1    Apr. 12, 2018

(51) Int. Cl.
| | | |
|---|---|---|
| A61B 17/70 | (2006.01) | |
| A61B 17/84 | (2006.01) | |
| A61B 17/86 | (2006.01) | |

(52) U.S. Cl.
CPC ........ *A61B 17/7052* (2013.01); *A61B 17/705* (2013.01); *A61B 17/7011* (2013.01); *A61B 17/7083* (2013.01); *A61B 17/842* (2013.01); *A61B 17/86* (2013.01); *A61B 17/7037* (2013.01)

(58) Field of Classification Search
CPC ....................................... A61B 17/7049–7052
USPC ................................ 606/250–253, 260, 278
See application file for complete search history.

(56) References Cited

U.S. PATENT DOCUMENTS

| | | | |
|---|---|---|---|
| 776,051 A | 11/1904 | Otto | |
| 1,920,821 A | 8/1933 | Wassenaar | |
| 4,733,657 A | 3/1988 | Kluger | |
| 4,957,495 A | 9/1990 | Kluger | |
| 5,219,349 A | 6/1993 | Krag et al. | |
| 6,171,311 B1 * | 1/2001 | Richelsoph | A61B 17/7049 606/250 |
| 6,416,515 B1 * | 7/2002 | Wagner | A61B 17/7034 606/250 |
| 7,416,553 B2 | 8/2008 | Patel et al. | |
| 7,578,822 B2 | 8/2009 | Rezach et al. | |
| 7,618,424 B2 | 11/2009 | Wilcox et al. | |
| 7,655,008 B2 | 2/2010 | Lenke et al. | |
| 7,655,025 B2 | 2/2010 | Ritland | |
| 7,794,464 B2 | 9/2010 | Bridwell et al. | |
| 7,914,536 B2 | 3/2011 | MacDonald et al. | |
| 7,922,731 B2 | 4/2011 | Schumacher et al. | |
| 8,021,399 B2 | 9/2011 | Ritland | |
| 8,157,806 B2 | 4/2012 | Frigg et al. | |

(Continued)

FOREIGN PATENT DOCUMENTS

| | | |
|---|---|---|
| DE | 3414374 C2 | 10/1985 |
| DE | 3807346 C1 | 6/1989 |

(Continued)

OTHER PUBLICATIONS

International Search Report and Written Opinion of the International Searching Authority, European Patent Office, PCT/US2017/055839, dated Feb. 1, 2018.

*Primary Examiner* — Nicholas J Plionis

(57) ABSTRACT

A spinal construct includes a body having a wall disposed between a first cavity and a second cavity. The second cavity being configured for disposal of an existing spinal implant. A rod is disposed with the first cavity and connectable with tissue. The rod is rotatable relative to the body. Systems, surgical instruments, implants and methods are disclosed.

20 Claims, 19 Drawing Sheets

(56) References Cited

U.S. PATENT DOCUMENTS

| | | | |
|---|---|---|---|
| 8,206,395 B2 | 6/2012 | McLean et al. | |
| 8,277,453 B2 | 10/2012 | Kave et al. | |
| 8,287,546 B2 | 10/2012 | King et al. | |
| 8,394,109 B2 | 3/2013 | Hutton et al. | |
| 8,430,916 B1 | 4/2013 | Winslow et al. | |
| 8,728,124 B2* | 5/2014 | Miller | A61B 17/7014 606/250 |
| 8,758,411 B1* | 6/2014 | Rayon | A61B 17/7004 606/259 |
| 2001/0034521 A1 | 10/2001 | Bailey et al. | |
| 2004/0034298 A1 | 2/2004 | Johnson et al. | |
| 2005/0021040 A1 | 1/2005 | Bertagnoli | |
| 2005/0228377 A1* | 10/2005 | Chao | A61B 17/7052 606/252 |
| 2006/0229616 A1 | 10/2006 | Albert et al. | |
| 2006/0241600 A1* | 10/2006 | Ensign | A61B 17/7005 81/52 |
| 2008/0119862 A1 | 5/2008 | Wicker et al. | |
| 2008/0294195 A1* | 11/2008 | Egli | A61B 17/7019 606/246 |
| 2009/0062857 A1 | 3/2009 | Ramsay et al. | |
| 2009/0281572 A1* | 11/2009 | White | A61B 17/7005 606/246 |
| 2010/0234892 A1* | 9/2010 | Mazda | A61B 17/705 606/276 |
| 2010/0246923 A1 | 9/2010 | Nathaniel et al. | |
| 2010/0292735 A1* | 11/2010 | Schlaepfer | A61B 17/1728 606/278 |
| 2010/0324599 A1 | 12/2010 | Montello et al. | |
| 2011/0172662 A1 | 7/2011 | Keilen | |
| 2011/0319939 A1 | 12/2011 | Kretzer et al. | |
| 2012/0071885 A1 | 3/2012 | Forton et al. | |
| 2013/0274808 A1* | 10/2013 | Larroque-Lahitette | A61B 17/7005 606/278 |
| 2013/0345754 A1* | 12/2013 | Doubler | A61B 17/7037 606/266 |
| 2015/0374414 A1* | 12/2015 | Dant | A61B 17/7049 606/250 |

FOREIGN PATENT DOCUMENTS

| | | |
|---|---|---|
| EP | 1590077 B1 | 11/2005 |
| WO | 1990002527 A1 | 3/1990 |
| WO | 2002076315 A1 | 10/2002 |
| WO | 2004014231 A1 | 2/2004 |
| WO | 2005107415 A2 | 11/2005 |
| WO | 2006094754 A1 | 9/2006 |
| WO | 2006118998 A1 | 11/2006 |
| WO | 2007092797 A1 | 8/2007 |
| WO | 2008155772 A1 | 12/2008 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes a body having a wall disposed between a first cavity and a second cavity. The second cavity being configured for disposal of an existing spinal implant. A rod is disposable with the first cavity and connectable with tissue. The rod is rotatable relative to the body. In some embodiments, systems, surgical instruments, implants and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
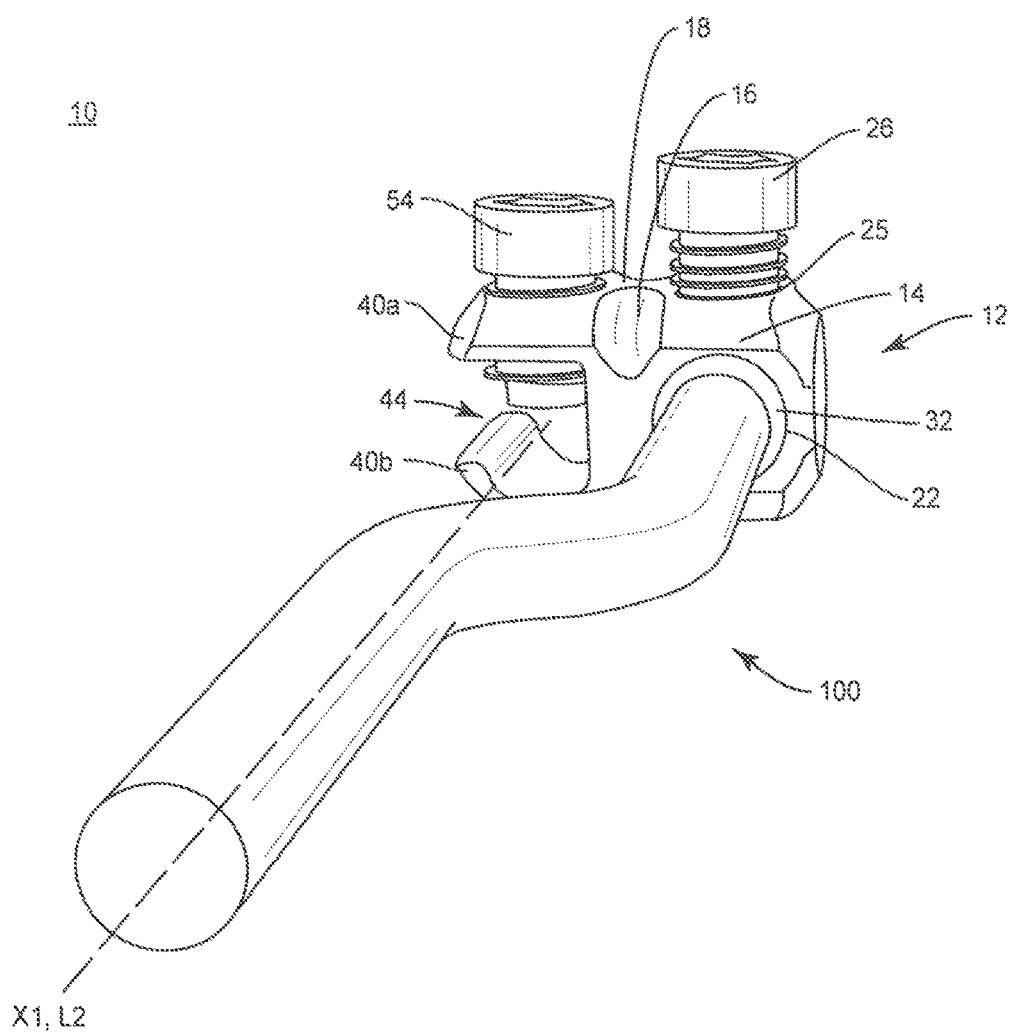
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a spinal construct comprising a connector. In some embodiments, the present surgical system includes a spinal construct comprising one or more revision minimally invasive surgical connectors. In some embodiments, the spinal construct includes a revision connector having an angularly adjustable rod and is configured to attach to one or more existing spinal constructs implanted with a body. In some embodiments, the spinal construct includes a connector having a multi-axial extension rod. In some embodiments, the spinal construct can be employed in a revision surgery to extend an existing screw and rod construct. In some embodiments, the spinal construct can be employed in a revision surgery to connect an existing spinal construct and extend the existing spinal construct to span one or more spinal levels.

In some embodiments, the present surgical system includes a spinal construct that can be employed in a revision surgery to connect to an existing rod implanted with a body. In some embodiments, the spinal construct and the existing spinal construct comprise an extension. In some embodiments, the spinal construct includes a connector having a multi-axial rod that is housed within the connector. In some embodiments, the multi axial rod includes a spherical end, which can freely rotate in a connector housing and be locked upon disposal in a selected position using a set screw.

In some embodiments, the present surgical system includes a spinal construct that can be employed in a revision surgery to connect to an existing bone screw and rod construct through a minimally invasive approach. In some embodiments, the spinal construct includes a side loading connector with a pre-assembled rod that comprises a multi-axial rod. In some embodiments, the multi-axial rod configuration includes a ring to retain the rod to the connector. In some embodiments, the pre-assembled side loading connector is placed through a tube or a retractor for extending an existing spinal construct. In some embodiments, the present surgical system includes a spinal construct having an adjustable rod geometry such that the rod is top-loaded to the connector after delivery of the connector to a surgical site.

In some embodiments, the present surgical system includes a spinal construct including a connector having two slots. In some embodiments, the connector includes a slot for holding an existing implanted rod and a slot that houses and locks a multi-axial extension rod. In some embodiments, the connector includes a multi-axial extension rod that provides rotation of the rod for disposal of the spinal construct in a selected orientation adjacent a surgical site. In some embodiments, the rod is rotated by leveraging a spherical shape of the multi-axial end of the spinal construct. In some embodiments, the connector includes at least one slot having a through hole.

In some embodiments, the present surgical system includes a spinal construct including a connector having a set screw that tightens a claw around an existing implanted rod. In some embodiments, the set screw opposes claw movement and forces the existing rod to maintain connection with the connector. In some embodiments, the present surgical system includes a spinal construct including a connector having a nut that is threaded into a bolt. In some embodiments, the bolt has jaws. In some embodiments, the nut is rotated clockwise to force the bolt upward. In some embodiments, the jaws of the bolt contact walls of the connector such that the resistance therebetween closes the jaws. In some embodiments, the resulting force locks the existing rod with the connector.

In some embodiments, the present surgical system includes a spinal construct including a connector that allows for clearance and housing of an existing rod. In some embodiments, the connector includes a hook like cut out formed in a body of the connector. In some embodiments, the connector can detect, identify, track, be guided and/or aligned with the existing rod using the cutout and a set screw that engages a top of the rod to lock the rod in a selected orientation.

In some embodiments, the present surgical system includes a spinal construct including a connector that is employed with a method of revision surgery, which includes the step of connecting the connector with an existing construct. In some embodiments, the connector includes a hook opening that faces an existing rod as the connector is delivered to a surgical site. In some embodiments, the connector engages the existing rod and is rotated so the set screw is oriented upward. In some embodiments, the connector is oriented and/or aligned so that the set screws will be facing upward when delivered to a surgical site. In some embodiments, the surgeon can manipulate the spinal construct and/or flick their wrist, left or right depending on orientation of the spinal construct to engage an existing rod. In some embodiments, the connector can be used to expand an existing construct without removing any previously implanted hardware. In some embodiments, the present surgical system is employed with a method of revision surgery to treat diseases where the discs above and/or below an existing construct begin to deteriorate and may be fused.

In some embodiments, the present surgical system includes a spinal construct including a top loading connector and an inserter. In some embodiments, the top loading connector and the inserter are employed with a method of revision surgery, which includes the step of detecting, identifying, tracking, being guided and/or aligned with an existing spinal construct. In some embodiments, the method includes the step of rotating the connector down to orient the set screw holes face upwards. In some embodiments, the method includes the step of inserting a set screw through the holes and onto the existing rod to fix the connector with the rod.

In some embodiments, the spinal construct includes a rod slot, such as, for example, a passageway configured for attachment with a spinal implant, such as, for example, a spinal rod mounted to vertebrae by, such as, for example, pedicle screws and/or hooks. In some embodiments, the spinal construct includes a second passageway configured for attachment with a spinal implant, such as, for example, a spinal rod to extend an existing construct to one or more adjacent levels. In some embodiments, the spinal construct includes a connector having a side loading passageway and a top loading passageway.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

Figure 2:
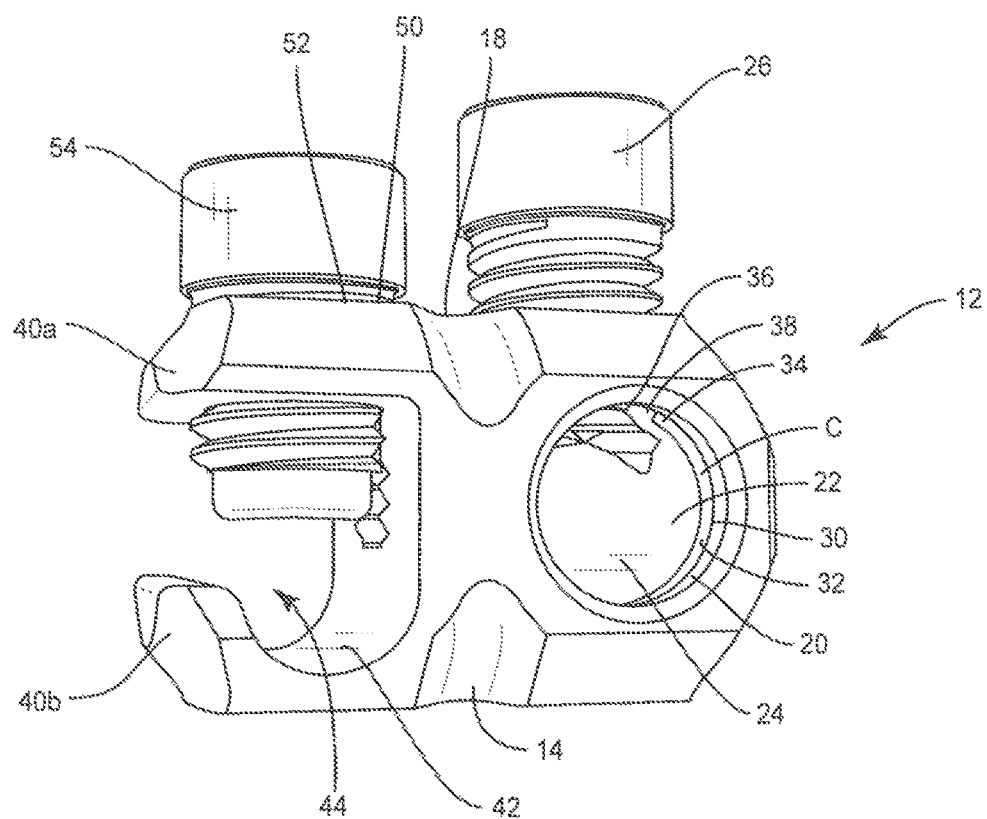
FIG. 2 is a perspective view of components of one embodiment of a system in accordance with the principles of the present disclosure.
Figure 3:
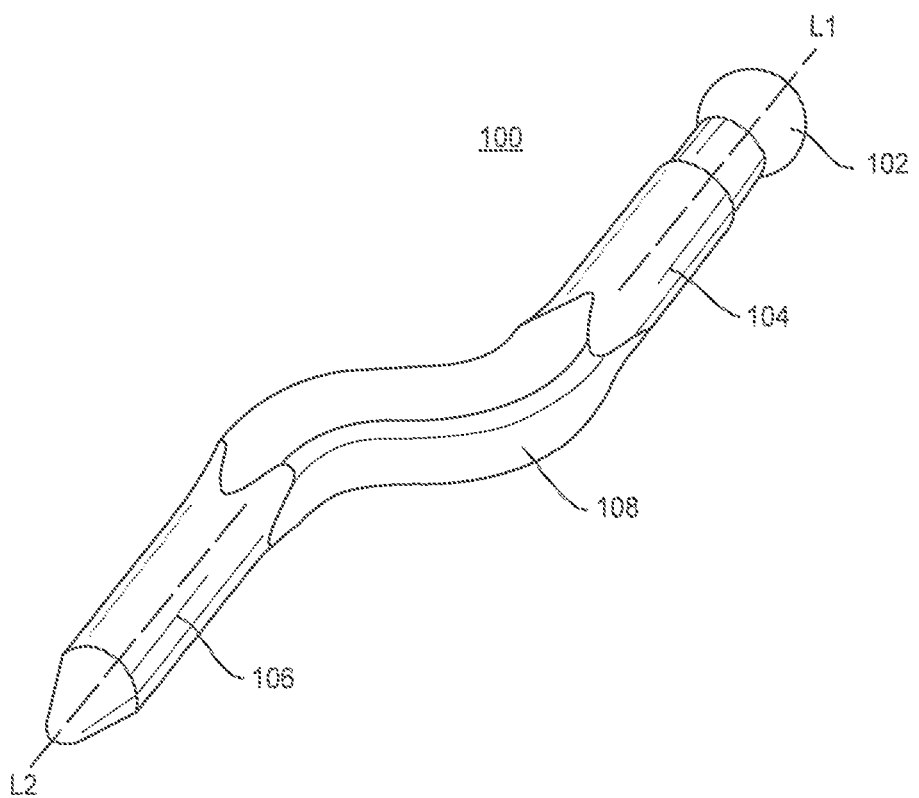
FIG. 3 is a perspective view of components of one embodiment of a system in accordance with the principles of the present disclosure.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with existing spinal constructs, which may include spinal implants such as one or more rods, fasteners, plates and connectors, attached with vertebrae in a revision surgery to manipulate tissue and/or correct a spinal disorder, as described herein. In some embodiments, one or more of the components of spinal implant system 10 can be employed in a revision surgery to connect an existing spinal construct and extend the existing spinal construct to span one or more spinal levels. Spinal implant system 10 comprises a spinal construct, such as, for example, a connector 12. In some embodiments, connector 12 is configured to extend an existing spinal implant without removing the existing spinal implant. In some embodiments, existing spinal constructs may include one or more implants connected or fixed with tissue in a prior or different surgical procedure, separate in time and/or over a duration of time in the same surgical procedure.

Connector 12 includes a body 14 having a surface 16 that defines a wall 18. Body 14 includes a mating element, such as, for example, a surface 20 that defines a portion of a cavity 22. Cavity 22 is configured for disposal of a head 102 of a rod 100, as described herein. In some embodiments, cavity 22 includes a surface 24 that defines a socket configured for disposal of head 102 in a multi-axial movement configuration, as described herein. In some embodiments, surface 24 defines a spheroidal joint with head 102 to facilitate multi-axial movement of rod 100 relative to connector 12, as described herein. In some embodiments, rod 100 is pre-assembled with connector 12 such that head 102 is enclosed by surface 24 within cavity 22. In some embodiments, a surface 24 defines an opening 25 that is threaded for engagement with a coupling member, such as, for example, a set screw 26 configured to fix rod 100 in a selected orientation relative to connector 12 and/or tissue, as described herein.

Surface 24 defines a cavity, such as, for example, a groove 30 configured for disposal of a band, such as, for example, a circumferential ring 32. Ring 32 includes a circumference C that extends between an end 34 and an end 36. Ends 34, 36 define an opening, such as, for example, a gap 38. Ring 32 is expandable and resilient between a contracted and/or capture orientation with rod 100 and an expanded orientation for pass through and/or release of rod 100, as described herein. Ring 32 facilitates engagement and connection of rod 100 with connector 12, as described herein.

Figure 4:
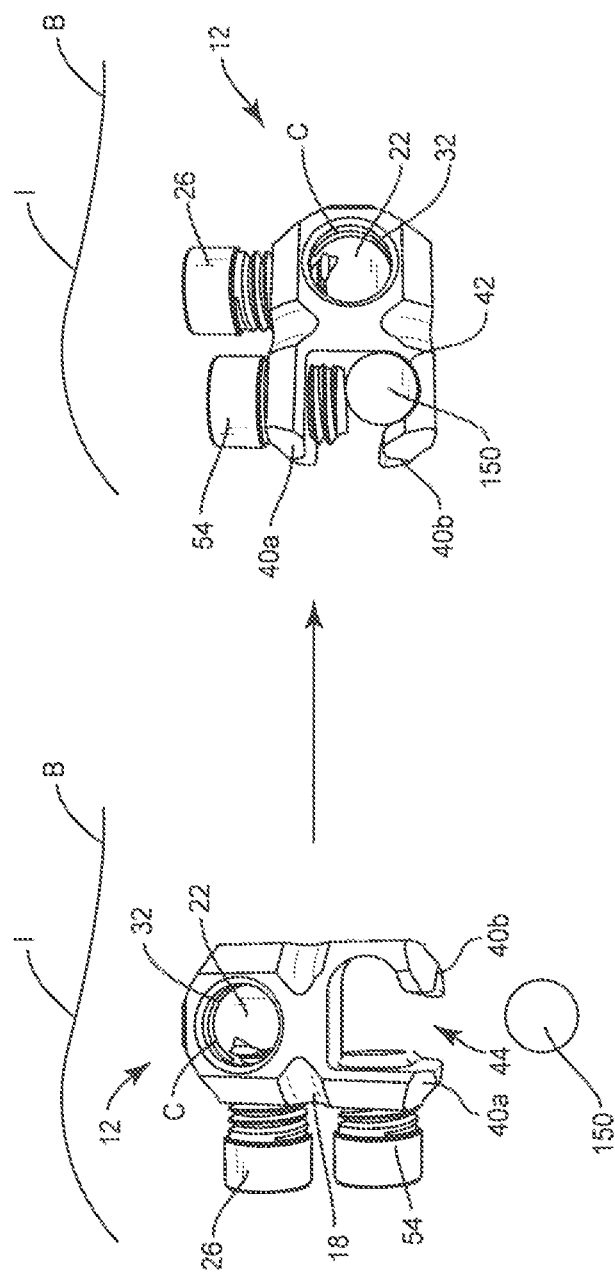
FIG. 4 is a perspective view of components of one embodiment of a system in accordance with the principles of the present disclosure disposed with a patient body.
Figure 5:
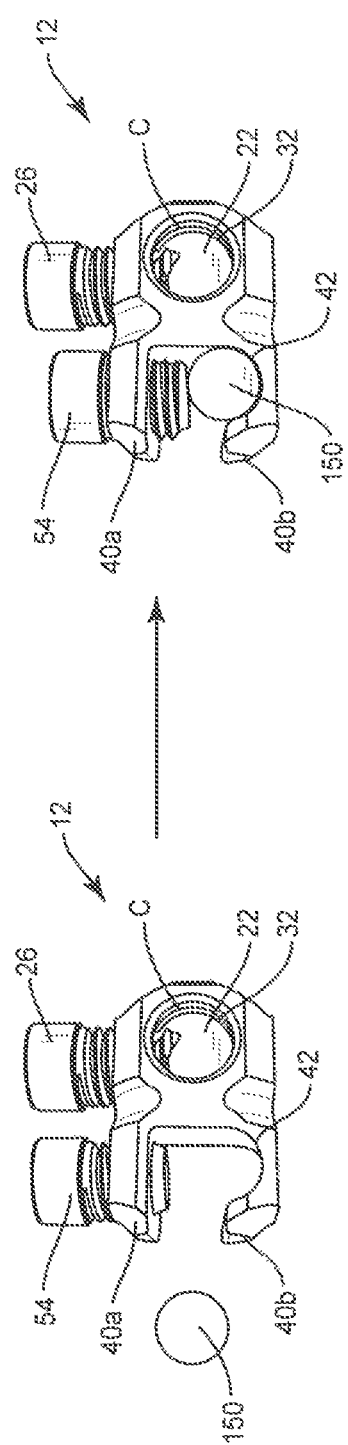
FIG. 5 is a perspective view of components of one embodiment of a system in accordance with the principles of the present disclosure disposed with a patient body.
Figure 6:
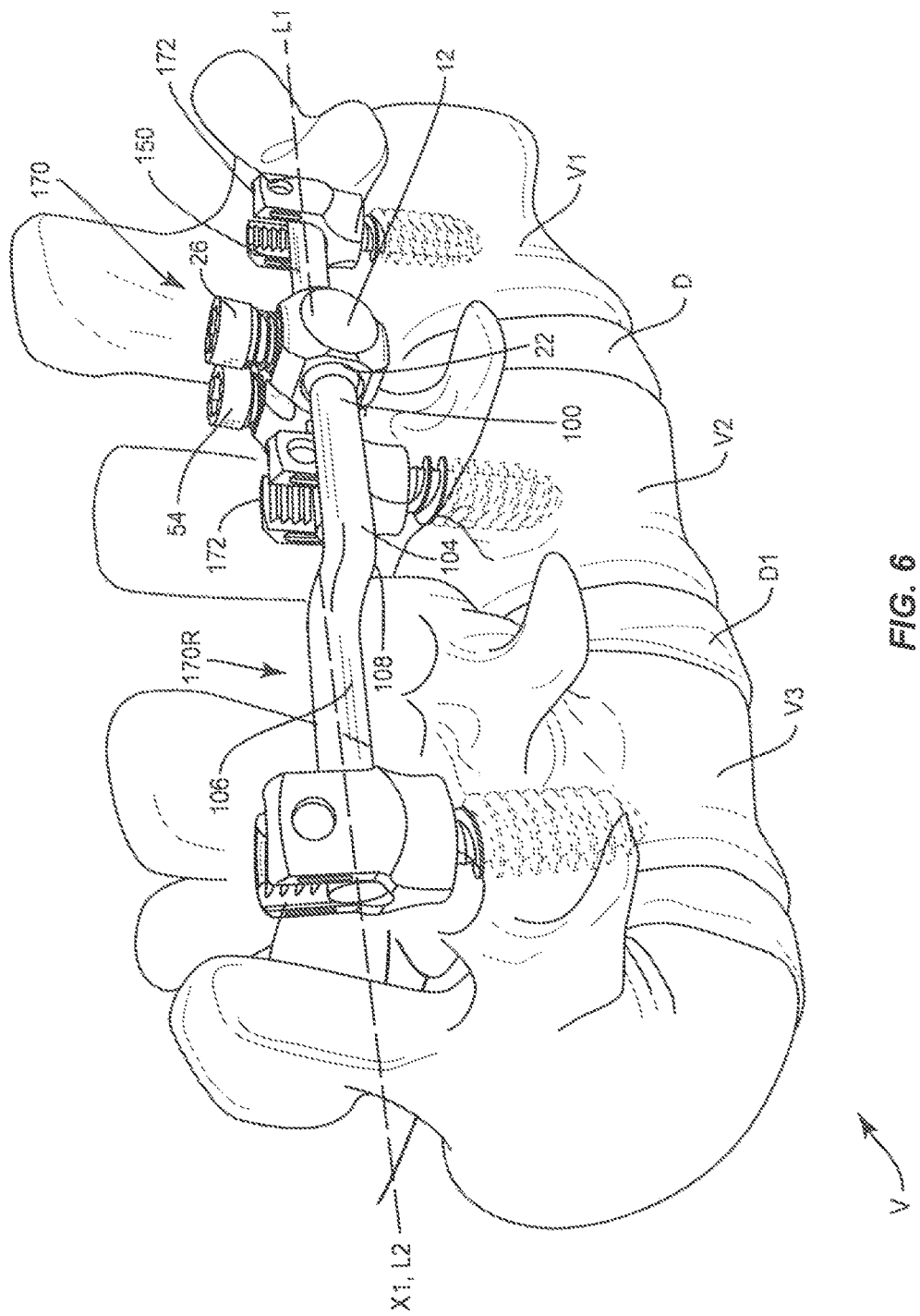
FIG. 6 is a perspective view of components of one embodiment of a system in accordance with the principles of the present disclosure disposed with vertebrae.

Wall 18 includes extensions 40a, 40b. Extensions 40a, 40b are disposed in a spaced apart relation. Extensions 40a, 40b extend perpendicular to wall 18. In some embodiments, extension 40a and/or extension 40b may be disposed at alternate orientations, relative to wall 18, such as, for example, transverse and/or other angular orientations such as acute or obtuse, coaxial and/or may be offset or staggered. Extensions 40a, 40b and a surface 42 of wall 18 define a cavity, such as, for example, a passageway 44. Passageway 44 extends along an axis X1, as shown in FIGS. 1 and 6. Passageway 44 is configured for disposal of an existing spinal implant, such as, for example, a spinal rod 150, as shown in FIGS. 4-6. Passageway 44 is configured for side and/or lateral loading of spinal rod 150 to connect spinal rod 150 with connector 12 for disposal along axis X1, as described herein. In some embodiments, surface 42 includes an arcuate configuration to facilitate engagement with spinal rod 150.

In some embodiments, passageway 44 is disposed separate and apart from cavity 22. In some embodiments, passageway 44 is disposed in a side by side orientation relative to cavity 22. In some embodiments, passageway 44 is disposed in a parallel orientation relative to cavity 22. In some embodiments, passageway 44 is disposed transverse to cavity 22. In some embodiments, passageway 44 may be disposed in various orientations, such as, for example, perpendicular, transverse and/or at angular orientations, such as acute or obtuse relative to cavity 22. In some embodiments, passageway 44 may be disposed offset or staggered from cavity 22. In some embodiments, passageway 44 may have various cross section configurations, such as, for example, oval, oblong, triangular, rectangular, square, polygonal, irregular, uniform, non-uniform, variable and/or tapered. In some embodiments, surface 42 may include gripping elements or surfaces that can be, for example, rough, arcuate, undulating, mesh, porous, semi-porous, dimpled and/or textured to facilitate engagement with spinal rod 150.

Body 14 includes a surface 50 that defines a cavity, such as, for example, an opening 52. Surface 50 is threaded and configured for disposal of a coupling member, such as, for example, a set screw 54. Set screw 54 is configured for engagement with spinal rod 150 to facilitate fixation and/or locking of spinal rod 150 with connector 12. Set screw 54 is disposable between a non-locking orientation such that spinal rod 150 is translatable relative to connector 12 and a locked orientation such that set screw 54 fixes spinal rod 150 with connector 12.

Rod 100 includes head 102 and a shaft 104 that defines an axis L1, as shown in FIG. 3. Head 102 includes a substantially spherical configuration and is configured for moveable disposal within cavity 22. Head 102 is configured to apply a force to ring 32 to move ring 32 between a contracted and/or capture orientation and an expanded orientation, as described herein. In some embodiments, head 102 defines a spheroidal joint with cavity 22 to facilitate multi-axial movement of rod 100 relative to connector 12, as described herein. Head 102 is configured to facilitate rotation of shaft 104 relative to connector 12 through a plurality of planes, for example, transverse, coronal and sagittal planes of a body, relative to connector 12.

In some embodiments, head 102 is slidably engageable with surface 24 and movable relative thereto such that shaft 104 is rotatable along a plurality of axes relative to connector 12 including rotation about axis L1. In some embodiments, head 102 may be disposed with surface 24 in alternate fixation configurations, such as, for example, friction fit, pressure fit, locking protrusion/recess, locking keyway and/or adhesive.

Shaft 104 extends from head 102 along axis L1. Rod 100 includes a shaft 106. Shaft 106 is connected with shaft 104 via a transition portion 108. Portion 108 is configured to orient shaft 106 along an axis L2. Axis L2 is disposed offset from axis L1. Portion 108 is configured to provide clearance for an existing spinal implant, as shown in FIG. 6. In some embodiments, upon engagement of connector 12 with the existing spinal rod 150, spinal rod 150 is disposed in alignment with shaft 106 such that axis L2 is coaxial with axis X1.

In some embodiments, connector 12 and rod 100 are configured to extend an existing spinal construct one or more spinal levels without removal of existing spinal rod 150 such that connector 12 allows for clearance and housing of existing spinal rod 150. Connector 12 includes an opening or cutout formed in body 14 such that connector 12 can detect, identify, track, be guided and/or aligned with existing spinal rod 150 using the cutout and set screw 54 that engages spinal rod 150 to lock spinal rod 150 in a selected orientation.

In one embodiment, as shown in FIG. 4, connector 12 is inserted such that passageway 44 faces spinal rod 150 for a top loading configuration as connector 12 is disposed with a patient body B. Upon engagement of surface 42 with spinal rod 150, connector 12 is rotated to orient set screws 26, 54 towards an incision I in patient body B for access by a surgical instrument, such as, for example, a driver. In one embodiment, as shown in FIG. 5, connector 12 is inserted in a side loading configuration such that set screws 26, 54 are disposed towards incision I in patient body B for access by a surgical instrument, such as, for example, a driver. Connector 12 is manipulated in a direction, such as, for example, to the left or to the right to engage surface 42 with spinal rod 150. In some embodiments, a surgeon can manipulate the spinal construct and/or flick their wrist, left or right depending on orientation of connector 12 to engage spinal rod 150.

In some embodiments, spinal implant system 10 can include one or a plurality of connectors 12 such as those described herein and/or fixation elements, which may be employed with a single vertebral level or a plurality of vertebral levels. In some embodiments, one or more connectors 12 may be engaged with vertebrae in various orientations, such as, for example, series, parallel, offset, staggered and/or alternate vertebral levels. In some embodiments, one or more connectors 12 may be employed with multi-axial screws, sagittal angulation screws, pedicle screws, mono-axial screws, uni-planar screws, fixed screws, anchors, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, such as, for example, a surgical treatment of an applicable condition or injury of an affected section of a spinal column and adjacent areas within a body. In some embodiments, spinal implant system 10 includes connector 12 employed in a surgical treatment such as a revision surgery to extend an existing spinal construct. In some embodiments, spinal implant system 10 includes connector 12 employed in a revision surgery to connect with an existing spinal construct and extend the existing spinal construct to span one or more spinal levels. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

For example, a surgical treatment may include adding length to an existing spinal construct 170 that includes spinal rod 150, as shown in FIG. 6, implanted with vertebrae V in a prior surgical procedure and spans one or more intervertebral discs. In the prior surgical procedure, spinal rod 150 is implanted spanning a single vertebral disc D to structurally fuse adjacent vertebrae V1, V2 with existing spinal construct 170, which includes bone screws 172 connected with spinal rod 150 to span intervertebral disc D. In one example, subsequent or different to the prior surgical procedure, an adjacent disc D1 develops a disorder for treatment. In some embodiments, the treatment of disc D1 includes connector 12 employed in a revision surgery to connect with spinal rod 150 to form a revised spinal construct 170R that extends to span spinal levels V1-V3, as described herein. In some embodiments, this configuration avoids disruption and tissue damage of the area of the prior surgical procedure, and reduction in healing and treatment duration.

In connection with the revision surgery, to treat a selected section of vertebrae V, including vertebrae V1, V2, V3, as shown in FIG. 6, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access an existing spinal construct 170 including implanted bone screws 172 and implanted spinal rod 150. The surgical pathway is utilized for implantation of components of spinal implant system 10. A preparation instrument (not shown) can be employed to prepare tissue surfaces of vertebrae V, as well as for aspiration and irrigation of a surgical region.

Connector 12 is disposed adjacent spinal rod 150. Connector 12 is manipulated to dispose and capture spinal rod 150 with passageway 44 from a side or lateral loading orientation, as described herein. Connector 12 and rod 100 are configured to extend existing spinal construct 170 to form a revised spinal construct 170R. Connector 12 is translatable relative to spinal rod 150 for positioning. Upon engagement of spinal rod 150 with surface 42, set screw 54 is rotated into engagement with a surface of spinal rod 150 to fix spinal rod 150 with connector 12.

Rod 100 is manipulated such that shaft 106 is disposed in alignment with axis X1 of spinal rod 150 such that axis L2 is coaxial with axis X1 to extend existing spinal implant 170 to an adjacent vertebral level. Portion 108 is configured to provide clearance for existing spinal construct 170 to facilitate alignment of shaft 106 and spinal rod 150. Set screw 54 is rotated into engagement with head 102 to fix rod 100 in position relative to existing spinal implant 170. In some embodiments, rod 100 is configured to share the load applied to spinal rod 150.

Spinal construct 170R extends existing spinal construct 170 from disc D and vertebrae V1, V2 to disc D1 and vertebrae V3, as shown in FIG. 6, without disruption of existing spinal construct 170. Spinal construct 170R is configured to structurally fuse adjacent vertebrae V2, V3 with existing spinal construct 170 to bridge disc D1. In some embodiments, rod 100 is configured to add support and strength to spinal implant system 10 along vertebrae V. In some embodiments, spinal construct 170R is adjustable to selectively span one or more vertebrae.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 7-10, spinal implant system 10, similar to the systems and methods described herein, includes a connector 312, similar to connector 12, which can be employed with an existing spinal construct, similar to that described herein, for example, spinal construct 170.

Connector 312 includes a body 314 having a surface 316 that defines a wall 318. Body 314 includes a surface 320 that defines a cavity 322, similar to cavity 22 described herein. Cavity 322 is configured for disposal of head 102 of rod 100, as described herein. In some embodiments, cavity 322 includes a surface 324 that defines a socket configured for disposal of head 102 in a multi-axial movement configuration, as described herein. In some embodiments, surface 324 defines a spheroidal joint to facilitate multi-axial movement of rod 100 relative to connector 312, as described herein. In some embodiments, rod 100 is pre-assembled with connector 312 such that head 102 is enclosed by surface 324 within cavity 322. In some embodiments, surface 324 defines an opening 325 that is threaded for engagement with a set screw 326 configured to fix rod 100 in a selected orientation relative to connector 312 and tissue, as described herein.

Surface 324 defines a groove 330 configured for disposal of a circumferential ring 332, similar to ring 32 herein. Ring 332 is expandable and resilient between a contracted and/or capture orientation, and an expanded orientation, as described herein. Ring 332 facilitates engagement of rod 100 with connector 312, as described herein.

Figure 7:
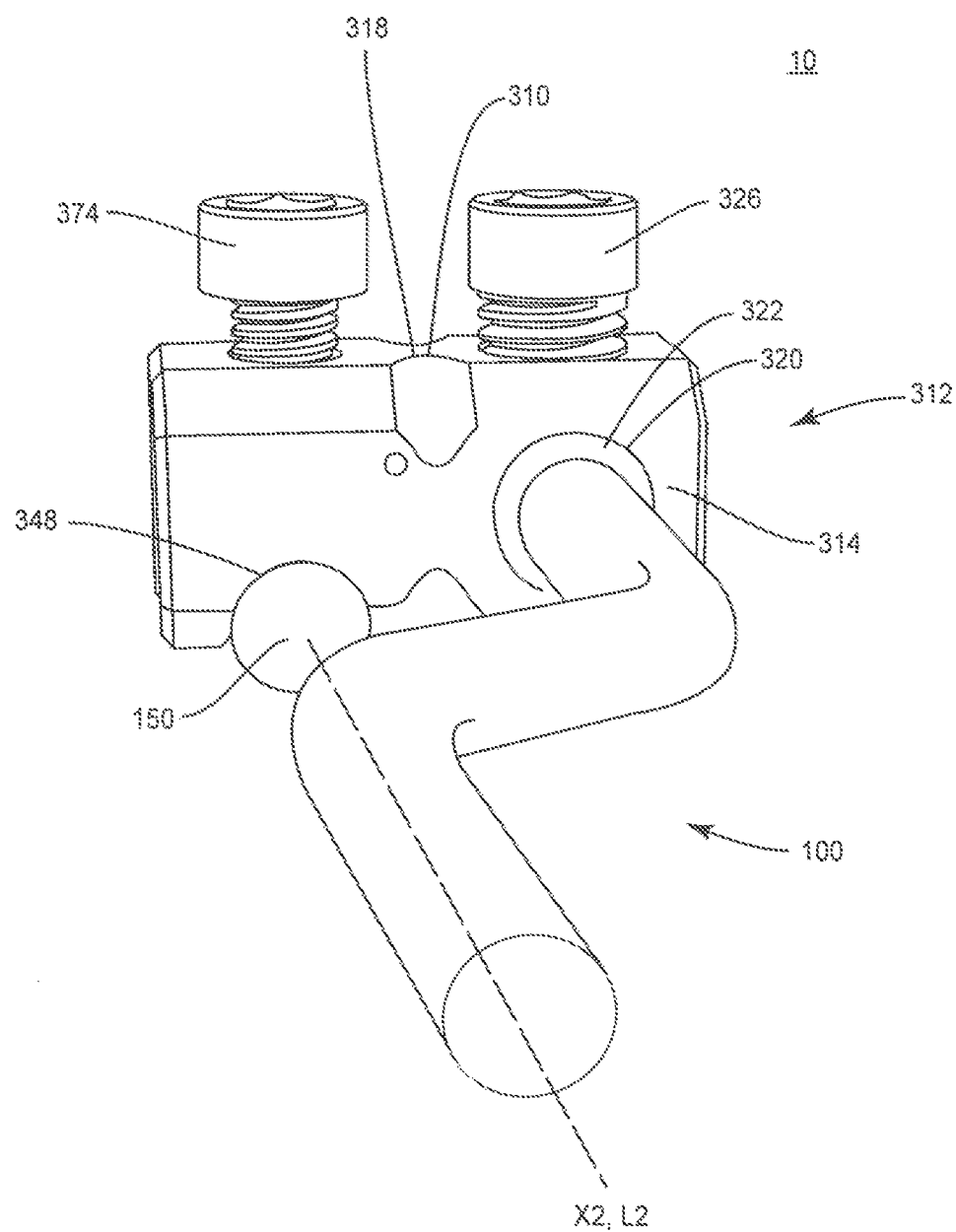
FIG. 7 is a perspective view of components of one embodiment of a system in accordance with the principles of the present disclosure.
Figure 8:
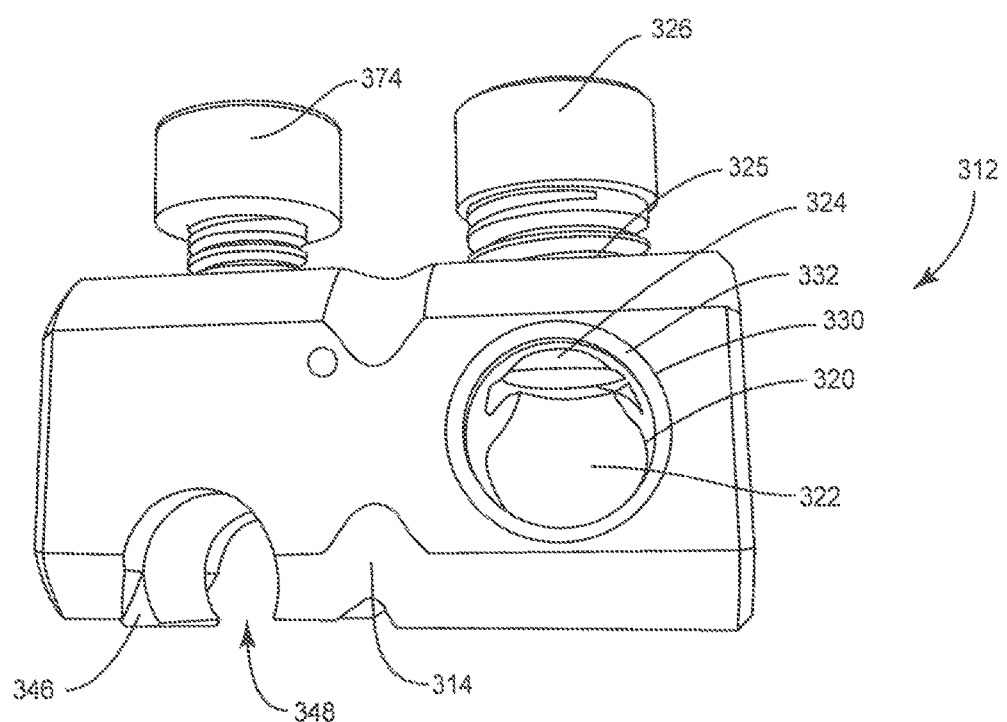
FIG. 8 is a perspective view of the components shown in FIG. 7.
Figure 10:
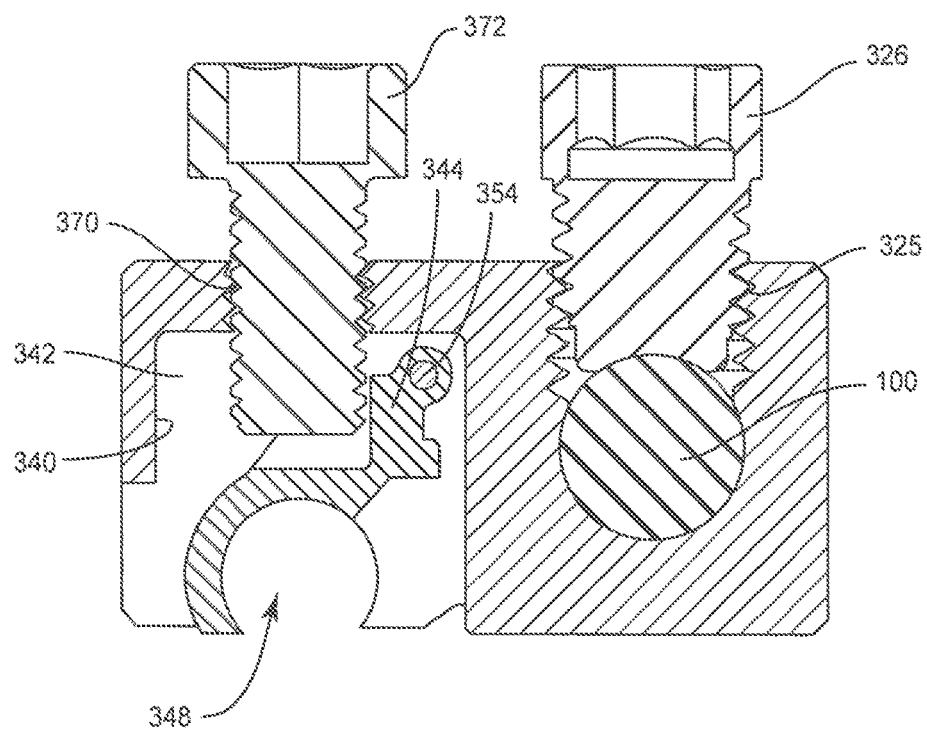
FIG. 10 is a cross section view of components of one embodiment of a system in accordance with the principles of the present disclosure.
Figure 11:
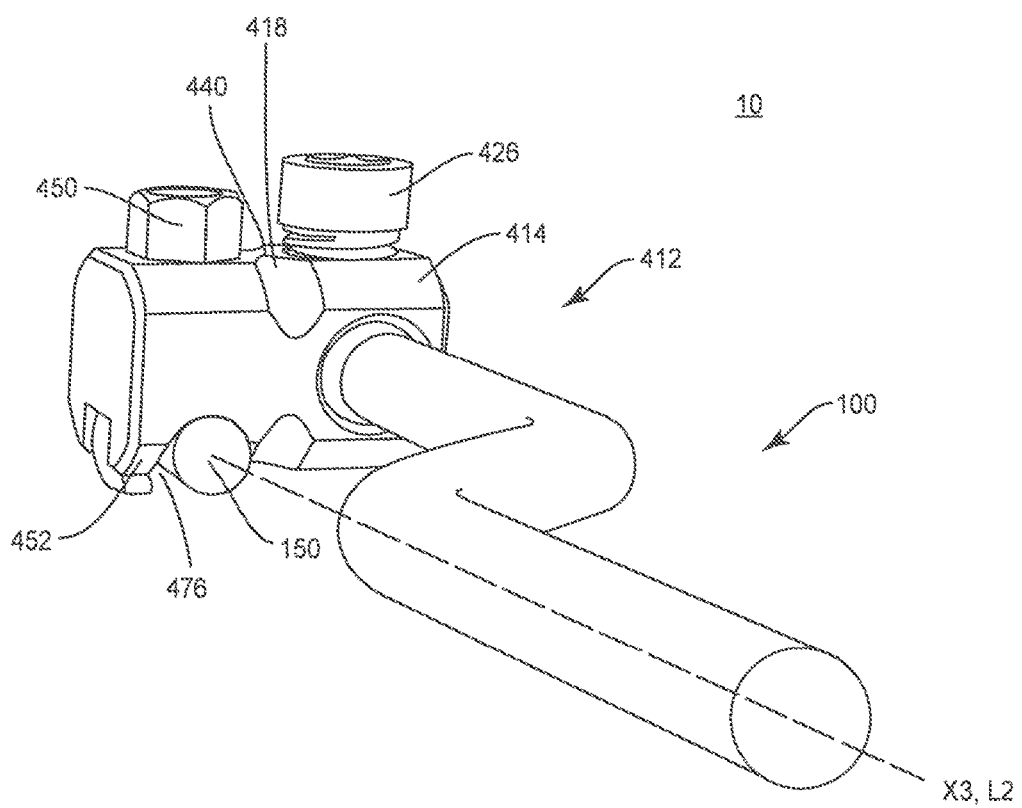
FIG. 11 is a perspective view of components of one embodiment of a system in accordance with the principles of the present disclosure.
Figure 12:
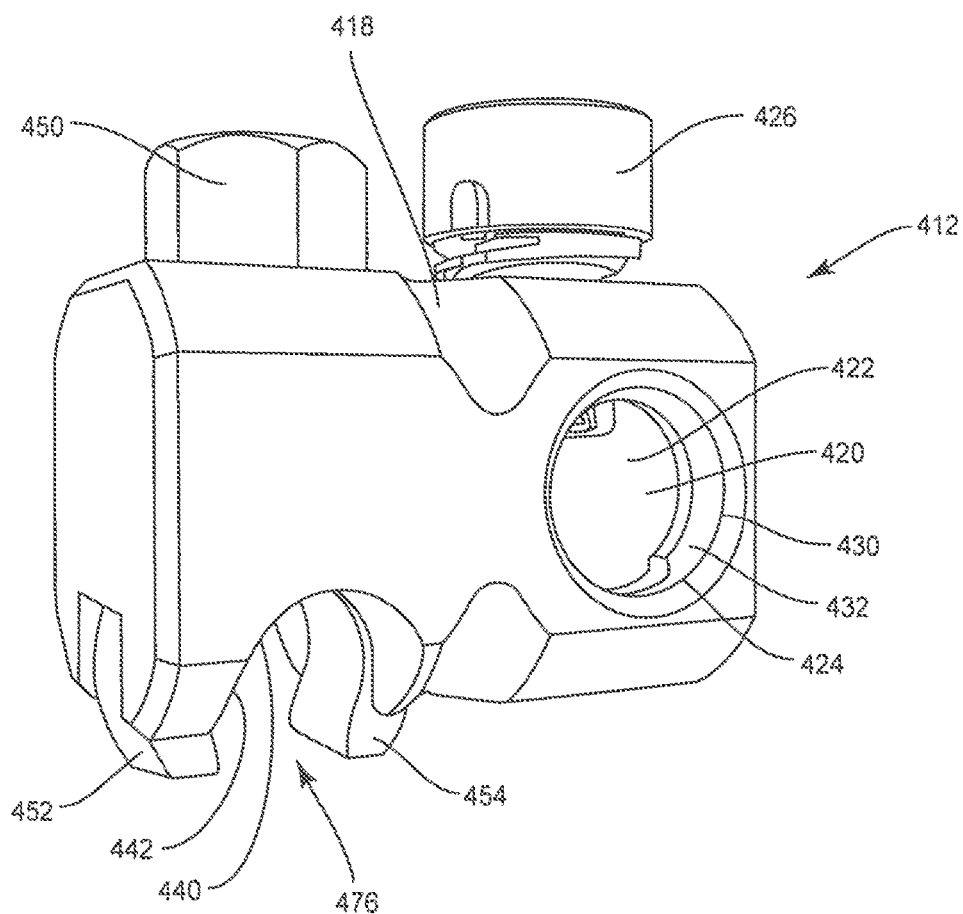
FIG. 12 is a perspective view of the components shown in FIG. 11.

Body 314 includes a surface 340 that defines a cavity 342, as shown in FIG. 10. Surface 340 includes protrusion, such as, for example, an arm 344 extending from surface 340. In some embodiments, arm 344 includes a hooked shaped wall 346 that defines a passageway 348 configured to capture spinal rod 150 within cavity 342. Passageway 348 extends along an axis X2, as shown in FIG. 7. Passageway 348 is configured for disposal of spinal rod 150. Passageway 348 is configured for side or lateral loading and capture of spinal rod 150 for disposal along axis X2, as described herein.

In some embodiments, arm 344 may extend from surface 340 in various orientations, such as, for example, perpendicular, transverse and/or at angular orientations, such as acute or obtuse. Arm 344 is configured for connection with body 314 such that arm 344 is rotatable relative to body 314. Arm 344 includes a surface 350 that defines an opening 352. Opening 352 is configured for disposal of a pin hinge 354. Arm 344 is configured to rotate about pin hinge 354 relative to body 314 to facilitate side loading and capture of spinal rod 150 to engage spinal rod 150 with connector 312.

Figure 9:
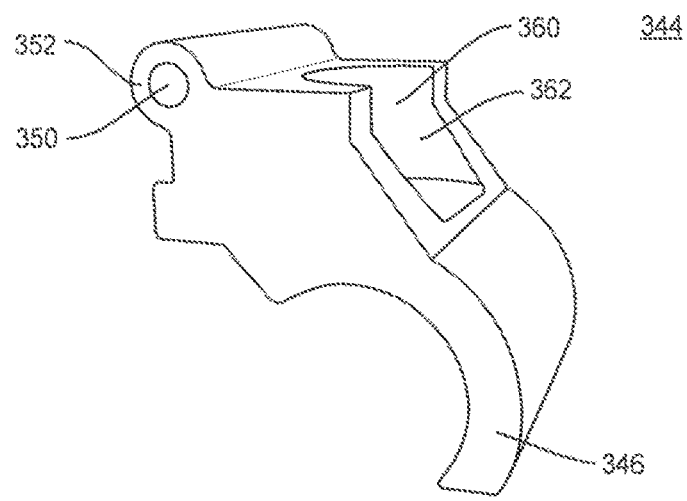
FIG. 9 is a perspective view of components of the system shown in FIG. 7.

Arm 344 includes a surface 360 that defines a cavity 362, as shown in FIG. 9. Cavity 362 is configured for disposal of a set screw 372 to facilitate engagement of spinal rod 150 with connector 312, as described herein. Engagement of set screw 372 with surface 360 is configured to resist and/or prevent rotation of arm 344.

Surface 340 defines an opening 370. A portion of surface 340 is threaded and configured for disposal of set screw 372. Set screw 372 is configured for engagement with arm 344 to facilitate fixation and/or locking of spinal rod 150 with connector 312. Set screw 372 is disposable between a non-locking orientation and a locked orientation. In the non-locking orientation, arm 344 is rotatable and spinal rod 150 is translatable relative to connector 312. In the locked orientation, set screw 372 engages surface 360 to resist and/or prevent rotation of arm 344 to fix spinal rod 150 with connector 312. Arm 344 is configured to rotate and tighten around spinal rod 150 upon disposal of set screw 372 in the locking orientation. In some embodiments, a surgical treatment includes connector 312 employed in a revision surgery to connect with an existing spinal construct, for example, spinal construct 170 including spinal rod 150, to form a revised spinal construct, for example, spinal construct 170R that extends to span one or more selected spinal levels, similar to that described herein.

In some embodiments, the compressive forces and/or friction forces applied by wall 346 may be directed in various orientations, such as, for example, perpendicular, transverse and/or at angular orientations, such as acute or obtuse. In some embodiments, wall 346 may include penetrating members. In some embodiments, wall 346 may include gripping elements or surfaces, such as, for example, rough, arcuate, undulating, mesh, porous, semi-porous, dimpled and/or textured to facilitate engagement with spinal rod 150.

In one embodiment, as shown in FIGS. 11-14, spinal implant system 10, similar to the systems and methods described herein, includes a connector 412, similar to connector 12, which can be employed with an existing spinal construct, similar to that described herein, for example, spinal construct 170.

Connector 412 includes a body 414 having a surface 416 that defines a wall 418. Body 414 includes a surface 420 that defines a cavity 422, similar to cavity 22 described herein. Cavity 422 is configured for disposal of head 102 of rod 100, as described herein. In some embodiments, cavity 422 includes a surface 424 that defines a socket configured for disposal of head 102 in a multi-axial movement configuration, as described herein. In some embodiments, surface 424 defines a spheroidal joint to facilitate multi-axial movement of rod 100 relative to connector 412, as described herein. In some embodiments, rod 100 is pre-assembled with connector 412 such that head 102 is enclosed by surface 424 within cavity 422. In some embodiments, surface 424 defines an opening 425 that is threaded for engagement with a set screw 426 configured to fix rod 100 in a selected orientation relative to connector 412 and tissue, as described herein.

Surface 424 defines a groove 430 configured for disposal of a circumferential ring 432, similar to ring 32 described herein. Ring 432 is expandable and resilient between a contracted and/or capture orientation, and an expanded orientation, as described herein. Ring 432 facilitates engagement of rod 100 with connector 412, as described herein.

Figure 13:
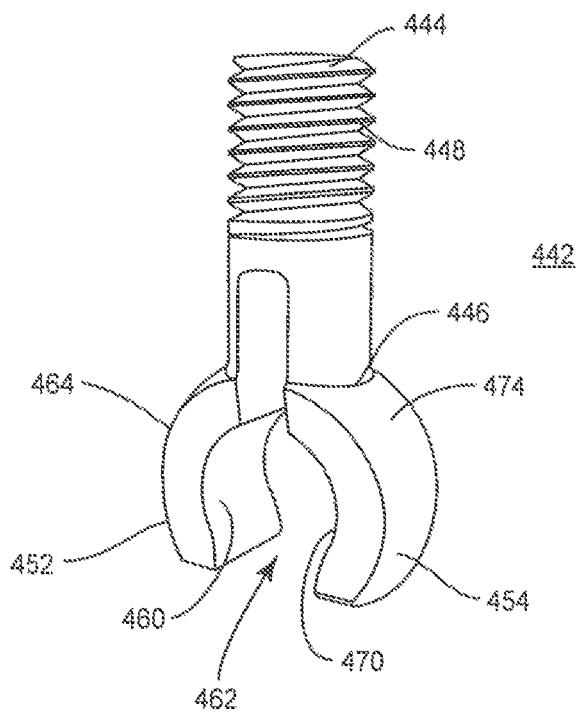
FIG. 13 is a perspective view of components of the system shown in FIG. 11.
Figure 14:
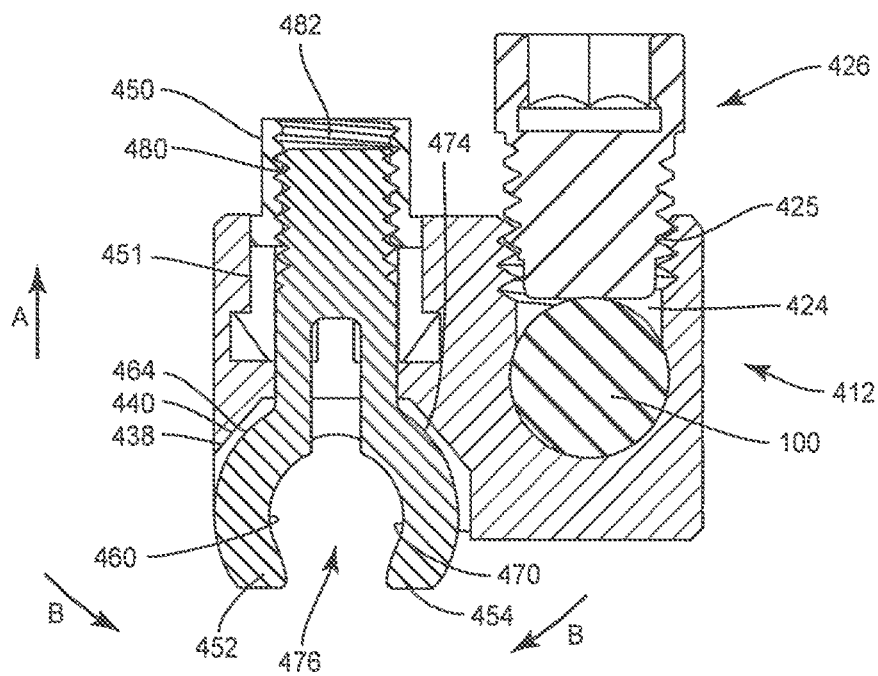
FIG. 14 is a cross section view of components of one embodiment of a system in accordance with the principles of the present disclosure.

Body 414 includes a surface 438 that defines a cavity 440, as shown in FIG. 14. Surface 438 is configured for engagement with a capture element, such as, for example, a bolt 442, as shown in FIG. 13. Bolt 442 extends between an end 444 and an end 446. End 444 includes a threaded portion 448 configured for engagement with a coupling member, such as, for example, a nut 450, as described herein. Nut 450 is configured to freely rotate within a cavity 451, as shown in FIG. 14. Nut 450 is configured to facilitate translation of bolt 442 to capture spinal rod 150 within cavity 440, as described herein.

End 446 includes extensions, such as, for example, an arm 452 and an arm 454, as shown in FIGS. 13 and 14. In some embodiments, arm 452 includes a hooked shaped configuration. Arm 452 includes a surface 460 that defines a portion of a support cavity 462. Cavity 462 is configured to capture at least a portion of spinal rod 150. Surface 460 is configured to surround and/or engage a portion of spinal rod 150. Arm 452 includes a surface 464 configured to engage surface 440 upon translation of bolt 442 within cavity 440. Translation of bolt 442 causes surface 438 to apply a force to surface 464 to pivot arm 452 to capture spinal rod 150.

In some embodiments, arm 454 includes a hooked shaped configuration. Arm 454 includes a surface 470 that defines a portion of support cavity 462. Cavity 462 is configured to capture at least a portion of spinal rod 150. Surface 470 is configured to surround and/or engage a portion of spinal rod 150. Arm 454 includes a surface 474 configured to engage surface 440 upon translation of bolt 442 within cavity 440. Translation of bolt 442 causes surface 438 to apply a force to surface 474 to pivot arm 454 to capture spinal rod 150.

Surfaces 460, 470 define a passageway 476 configured to capture spinal rod 150 within cavity 440. Passageway 476 extends along an axis X3, as shown in FIG. 14. Passageway 476 is configured for disposal of spinal rod 150. Passageway 476 is configured for side loading and capture of spinal rod 150 for disposal along axis X3, as described herein.

Arms 452, 454 are configured for relative movement to capture spinal rod 150, as described herein. In some embodiments, arms 452, 454 are resiliently biased to an open configuration and are movable to a closed configuration to capture spinal rod 150, as described herein.

Nut 450 includes a surface 480 that defines an opening 482. Opening 482 is configured for engagement with threaded portion 448. Nut 450 rotates to engage threaded portion 448 and draw bolt 442, in a direction shown by arrow A in FIG. 14, to axial translate bolt 442 relative to body 414. Translation of bolt 442 moves arms 452, 454, in a direction shown by arrows B in FIG. 14, into a capture configuration to capture spinal rod 150. Surface 438 applies a force to arms 452, 454 to contract and/or compress arms 452, 454 around spinal rod 150. In some embodiments, a surgical treatment includes connector 412 employed in a revision surgery to connect with an existing spinal construct, for example, spinal construct 170 including spinal rod 150, to form a revised spinal construct, for example, spinal construct 170R that extends to span one or more selected spinal levels, similar to that described herein.

Figure 15:
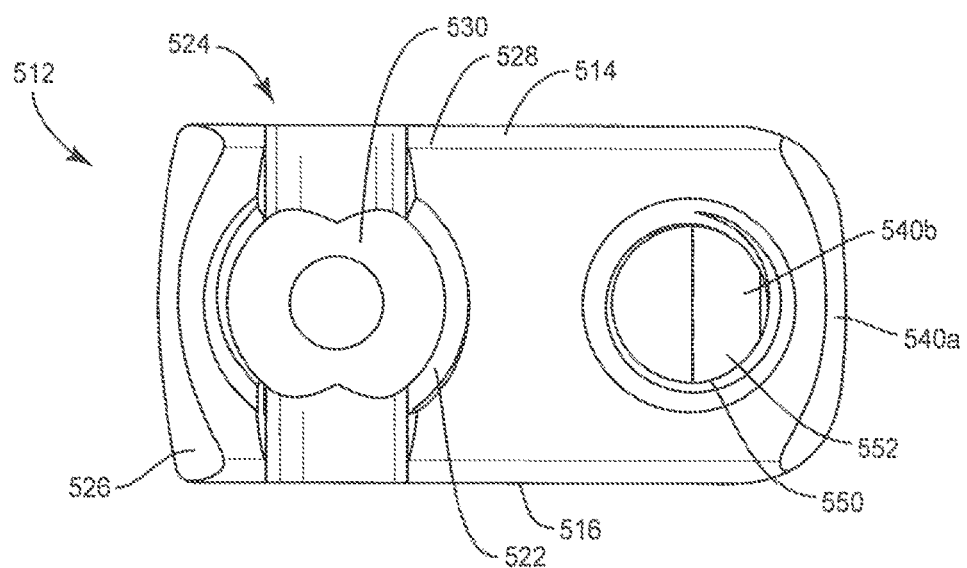
FIG. 15 is an end view of components of one embodiment of a system in accordance with the principles of the present disclosure.
Figure 16:
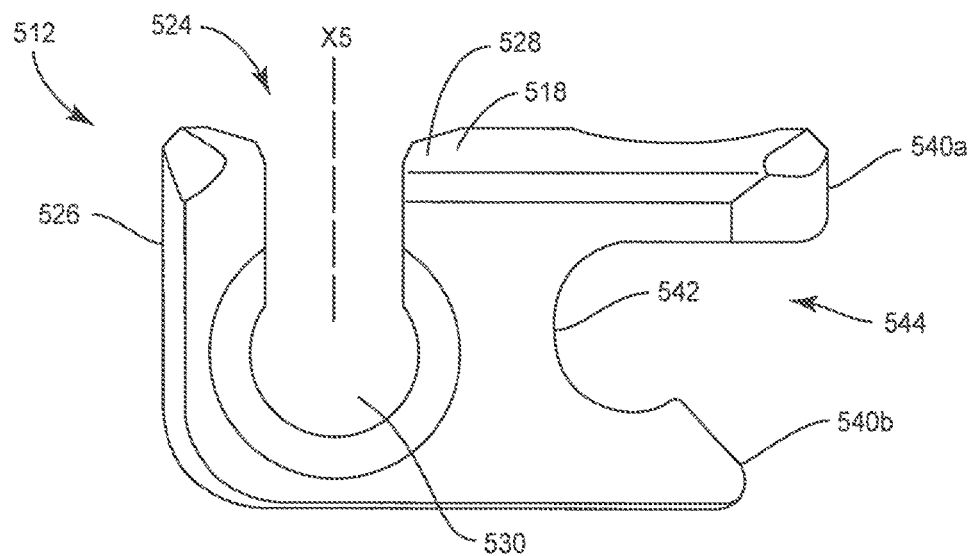
FIG. 16 is a side view of the components shown in FIG. 15.
Figure 17:
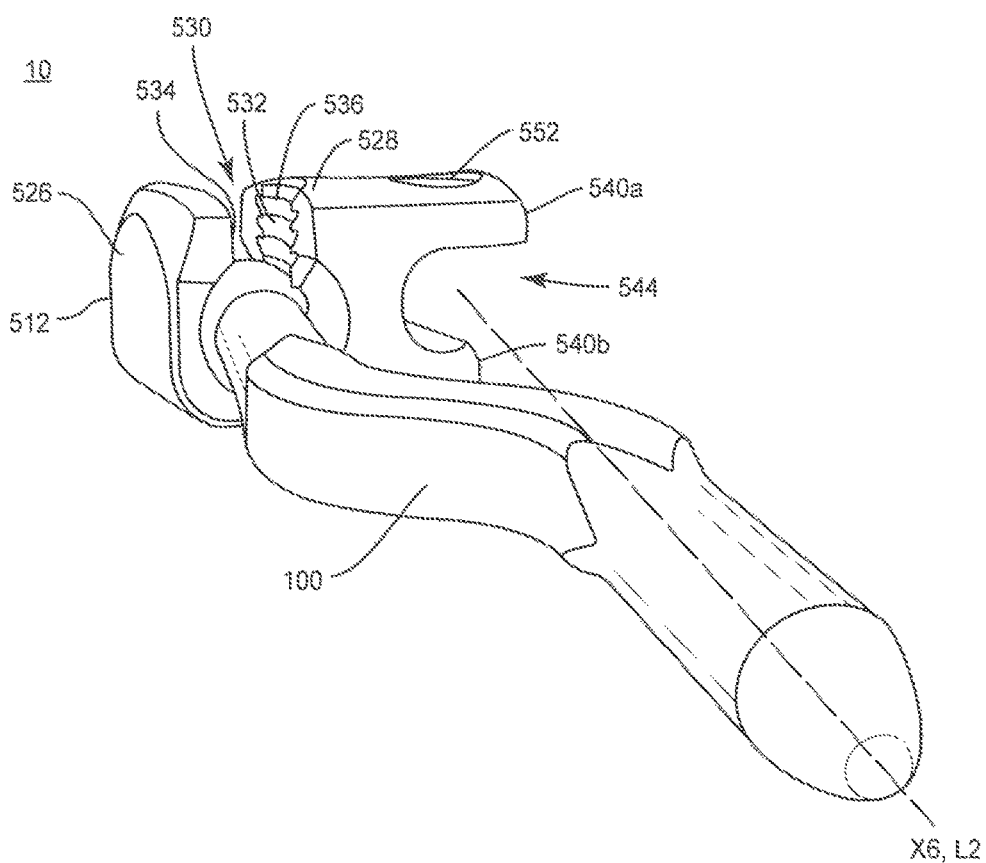
FIG. 17 is a perspective view of components of one embodiment of a system in accordance with the principles of the present disclosure.

In one embodiment, as shown in FIGS. 15-17, spinal implant system 10, similar to the systems and methods described herein, includes a connector 512, similar to connector 12, which can be employed with an existing spinal construct, similar to that described herein, for example, spinal construct 170.

Connector 512 includes a body 514 having a surface 516 that defines a wall 518. Wall 518 includes a surface 522 that defines a portion of a cavity, such as for example, a receiver 524. Receiver 524 includes a pair of spaced apart arms 526, 528 that define a passageway 530 therebetween. Passageway 530 is configured for top loading of rod 100, as shown in FIG. 17. Arms 526, 528 each extend parallel to an axis X5, as shown in FIG. 16.

Passageway 530 is substantially U-shaped. Receiver 524 includes an inner surface 532. A portion of surface 532 includes a thread form 534 located adjacent arm 526 and a thread form 536 located adjacent arm 528. Thread forms 534, 536 are each configured for engagement with a coupling member, such as, for example, a set screw (not shown), to retain rod 100 within receiver 524.

Wall 518 includes extensions 540a, 540b. Extensions 540a, 540b are disposed in a spaced apart relation. Extensions 540a, 540b extend perpendicular to wall 518. Extensions 540a, 540b and a surface 542 of wall 518 define a passageway 544. Passageway 544 extends along an axis X6, as shown in FIG. 17. Passageway 544 is configured for disposal of spinal rod 150. Passageway 544 is configured for side loading of spinal rod 150, as described herein. In some embodiments, surface 542 includes an arcuate configuration to facilitate engagement with spinal rod 150.

Body 514 includes a surface 550 that defines an opening 552. Surface 550 is threaded and configured for disposal of a set screw (not shown). The set screw is configured for engagement with spinal rod 150 to facilitate fixation and/or locking of spinal rod 150 with connector 512, as described herein. In some embodiments, a surgical treatment includes connector 512 employed in a revision surgery to connect with an existing spinal construct, for example, spinal construct 170 including spinal rod 150, to form a revised spinal construct, for example, spinal construct 170R that extends to span one or more selected spinal levels, similar to that described herein.

Figure 18:
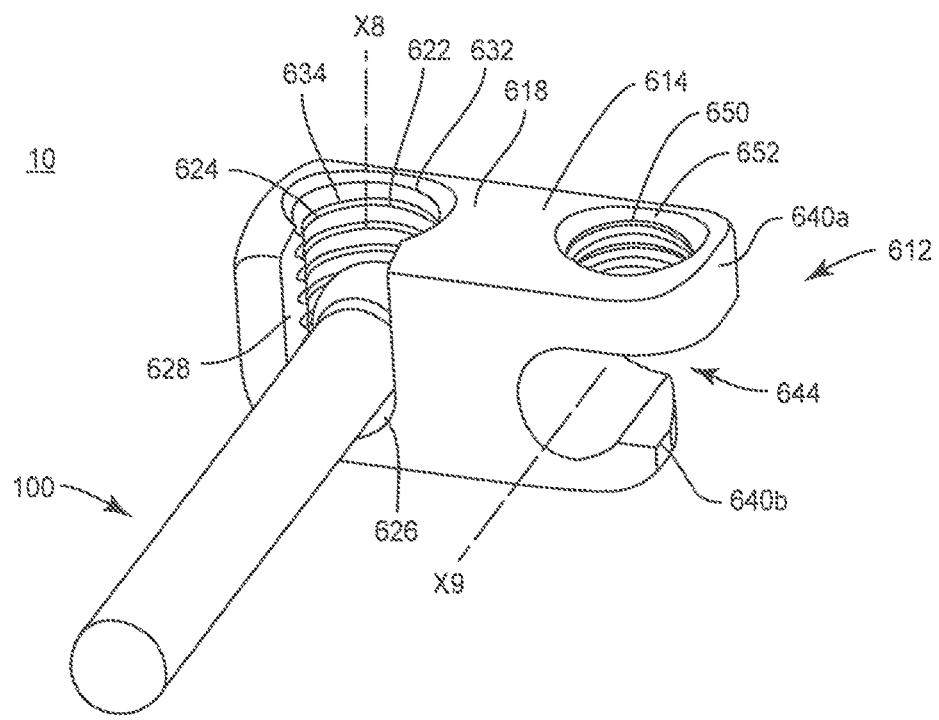
FIG. 18 is a perspective view of components of one embodiment of a system in accordance with the principles of the present disclosure.
Figure 19:
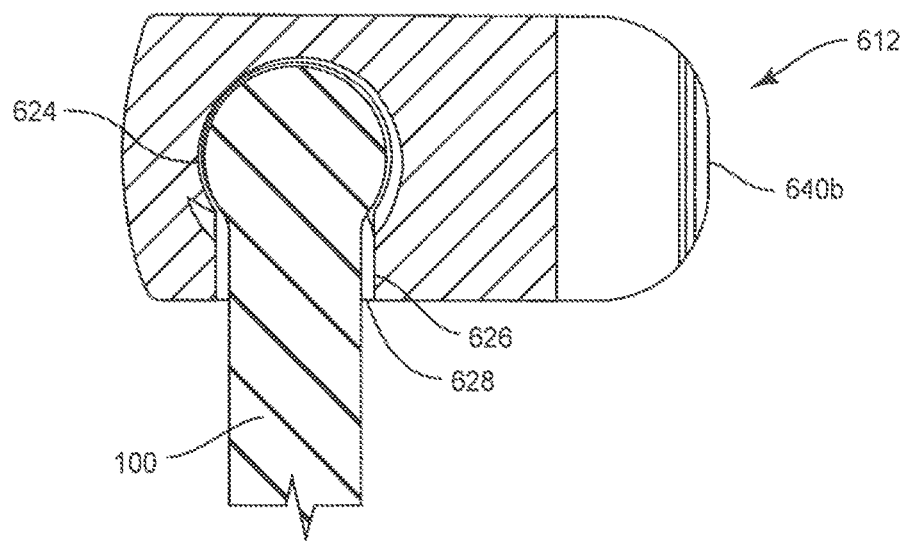
FIG. 19 is a cross section view of the components shown in FIG. 18.
Figure 20:
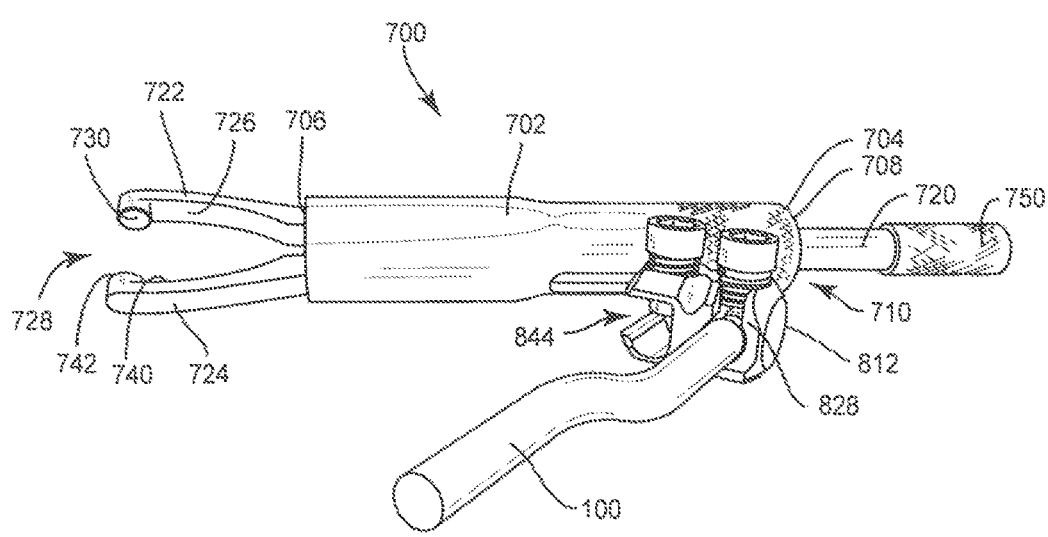
FIG. 20 is a perspective view of components of one embodiment of a system in accordance with the principles of the present disclosure.

In one embodiment, as shown in FIGS. 18 and 19, spinal implant system 10, similar to the systems and methods described herein, includes a connector 612, similar to connector 12, which can be employed with an existing spinal construct, similar to that described herein, for example, spinal construct 170.

Connector 612 includes a body 614 having a surface 616 that defines a wall 618. Wall 618 includes a surface 622 that defines a portion of a cavity, such as for example, a receiver 624. Receiver 624 is configured for disposal of a portion of head 102 of rod 100, as shown in FIG. 18. Receiver 624 includes a surface 626 that defines an opening 628. Opening 628 extends along an axis X8. Opening 628 is configured to facilitate top loading of rod 100 with connector 612, as shown in FIG. 18. In some embodiments, surface 626 is configured for engagement with a surgical instrument to facilitate insertion of connector 612, as described herein.

Receiver 624 includes an inner surface 632. A portion of surface 632 includes a thread form 634. Thread form 634 is configured for engagement with a coupling member, such as, for example, a set screw (not shown), to retain rod 100 within receiver 624.

Body 614 includes a surface 636. In some embodiment, surface 636 is configured for a friction fit engagement with a portion of a surgical instrument, as described herein. In some embodiments, surface 636 may include a cavity, such as, for example, a detent configured for engagement with the surgical instrument.

Wall 618 includes extensions 640a, 640b. Extensions 640a, 640b are disposed in a spaced apart relation. Extensions 640a, 640b extend perpendicular to wall 618. Extensions 640a, 640b and a surface 642 of wall 618 define a passageway 644. Passageway 644 extends along an axis X9, as shown in FIG. 18. Passageway 644 is configured for disposal of spinal rod 150, as described herein. Passageway 644 is configured for side loading of spinal rod 150, as described herein. In some embodiments, surface 642 includes an arcuate configuration to facilitate engagement with spinal rod 150.

Body 614 includes a surface 650 that defines an opening 652. Surface 650 is threaded and configured for disposal of a set screw (not shown). The set screw is configured for engagement with spinal rod 150 to facilitate fixation and/or locking of spinal rod 150 with connector 612, as described herein. In some embodiments, a surgical treatment includes connector 612 employed in a revision surgery to connect with an existing spinal construct, for example, spinal construct 170 including spinal rod 150, to form a revised spinal construct, for example, spinal construct 170R that extends to span one or more selected spinal levels, similar to that described herein.

In one embodiment, as shown in FIGS. 20-23, spinal implant system 10, similar to the systems and methods described herein, includes a connector 812, similar to connector 612, which can be employed with an existing spinal construct, similar to that described herein, for example, spinal construct 170, and a surgical instrument, such as, for example, an inserter 700. Connector 812 is configured for engagement with inserter 700.

Inserter 700 includes a body, such as, for example, a sleeve 702. Sleeve 702 extends between a proximal end 704 and a distal end 706. Sleeve 702 includes a surface 708 that defines a channel 710 extending between ends 704, 706. In some embodiments, sleeve 702 may have various configurations including, for example, round, oval, polygonal, irregular, consistent, variable, uniform and non-uniform.

Surgical instrument 700 includes a part 720 that extends within channel 720. Part 720 includes a distal end having an extension, such as, for example, an arm 722 and an extension, such as, for example, an arm 724. Arm 722 includes a surface 726 that defines a portion of a cavity 728 configured for disposal of connector 812. Surface 726 includes a protrusion 730. Protrusion 730 is configured for disposal within an opening 828, similar to opening 628 described herein. In some embodiments, a surface 826, similar to surface 626 described herein, forms a friction fit engagement with protrusion 730 to facilitate engagement. Arm 724 includes a surface 740 that defines a portion of cavity 728 configured for disposal of connector 812. Surface 740 includes a protrusion 742. In some embodiments, protrusion 742 is configured for disposal within opening 828. In some embodiments, surface 826 forms a friction fit engagement with protrusion 742 to facilitate engagement. In some embodiments, all or only a portion of protrusions 730, 742 may be alternately configured, such as, for example, uniform, non-uniform, offset, staggered, undulating, arcuate, variable and/or tapered.

Figure 21:
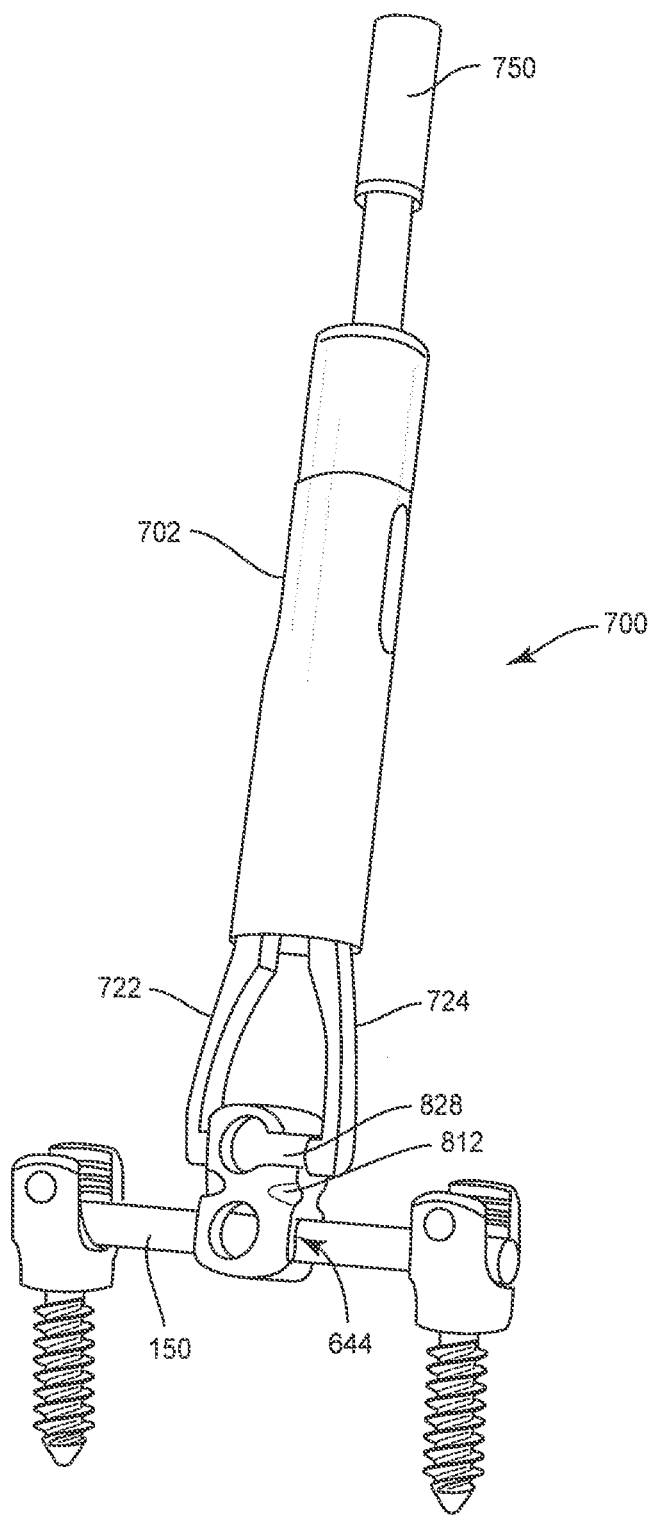
FIG. 21 is a perspective view of components of one embodiment of a system in accordance with the principles of the present disclosure.
Figure 22:
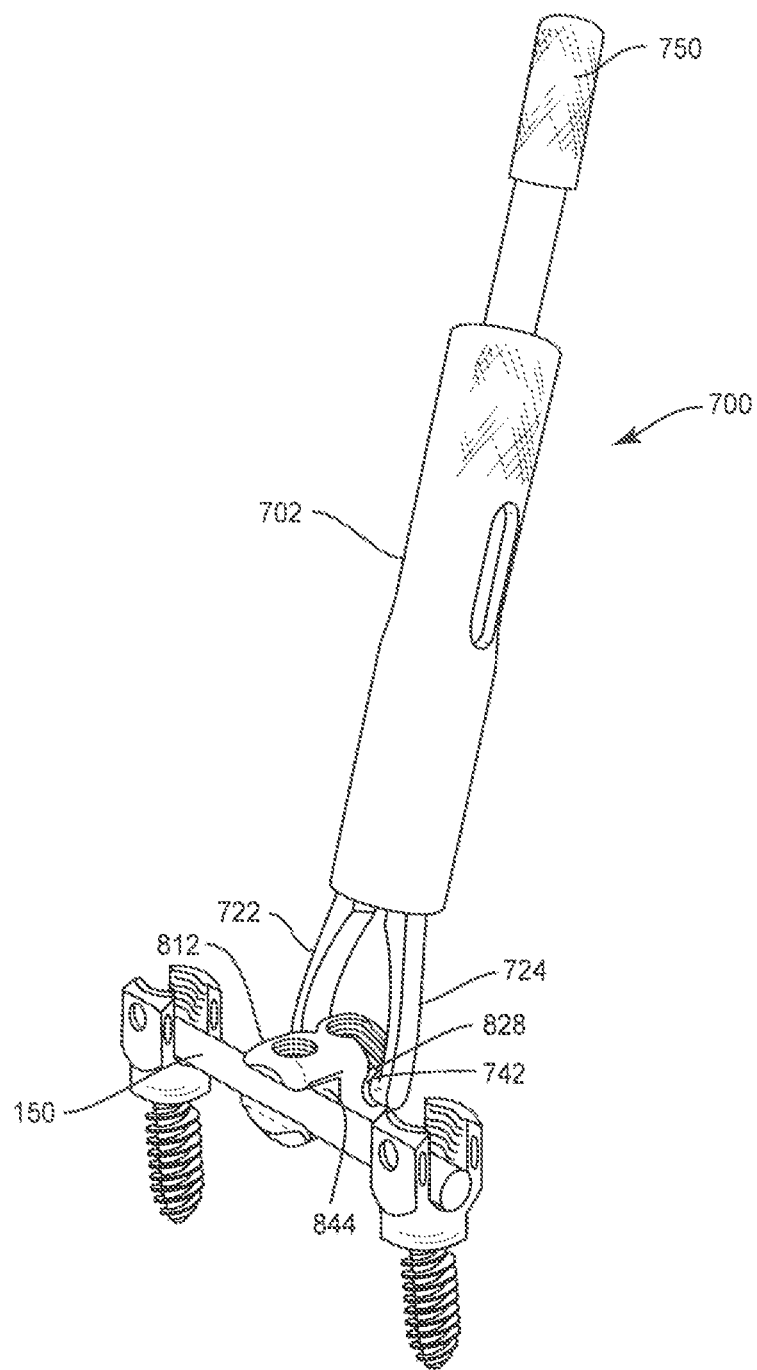
FIG. 22 is a perspective view of components of one embodiment of a system in accordance with the principles of the present disclosure.
Figure 23:
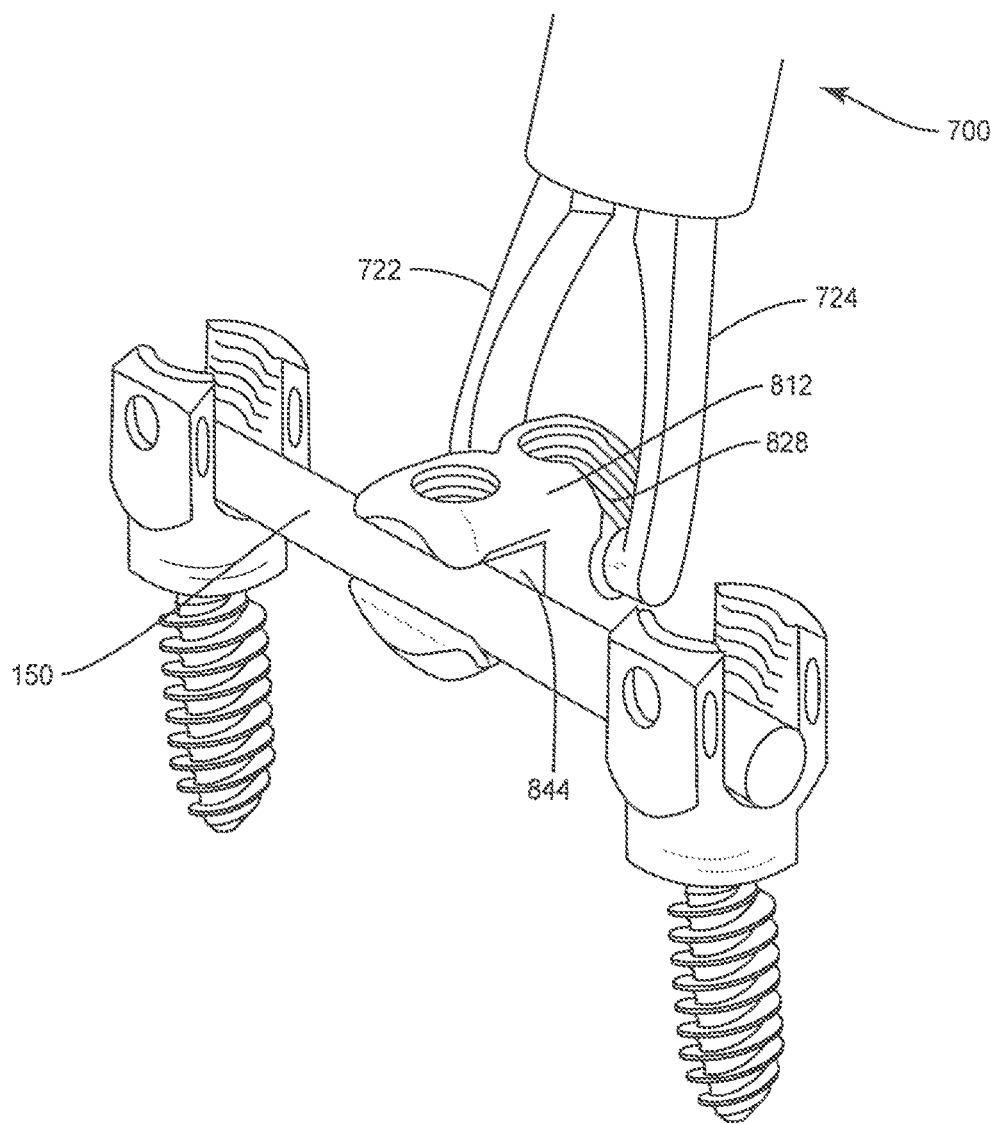
FIG. 23 is a perspective view of components of one embodiment of a system in accordance with the principles of the present disclosure.

Arms 722, 724 are engageable with an actuator, such as, for example, a knob 750. Knob 750 is configured to position arms 722, 724 to capture connector 812. Inserter 700 is configured to orient a passageway 844, similar to passageway 644 described herein, into alignment with spinal rod 150 for top loading capture of spinal rod 150. Connector 812 is rotated to provide access to the set screws to facilitate fixation of spinal rod 150 and rod 100 with connector 812, as shown in FIGS. 21-23. In some embodiments, a surgical treatment includes connector 812 and inserter 700 employed in a revision surgery to connect with an existing spinal construct, for example, spinal construct 170 including spinal rod 150, to form a revised spinal construct, for example, spinal construct 170R that extends to span one or more selected spinal levels, similar to that described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a body including opposite first and second sidewalls, the body defining a first cavity and a second cavity configured for disposal of an existing spinal implant, the body including a circular opening in communication with the first cavity, the circular opening extending through the first sidewall, the second sidewall being free of any openings in communication with the first cavity, the body including opposite top and bottom walls each extending from the first sidewall to the second sidewall, the body including a passageway extending through the top wall and in communication with the first cavity;
   a rod including a portion extending through the circular opening, the portion of the rod engaging an inner surface of the second sidewall to allow the rod to rotate relative to the body; and
   a coupling member extending through the passageway and including a first end surface and an opposite second end surface, the first end surface having a diameter greater than a diameter of the second end surface, the second end surface being concave and positioned within the first cavity to engage the portion of the rod.

2. A spinal construct as recited in claim 1, wherein the rod includes a head and a shaft that is rotatable about one or a plurality of axes relative to the body.

3. A spinal construct as recited in claim 1, wherein the rod includes a head and a shaft, the body and the head forming a spheroidal joint.

4. A spinal construct as recited in claim 1, wherein the diameter of the first end surface is greater than a diameter of the passageway.

5. A spinal construct as recited in claim 1, wherein the rod includes a head and a shaft that is connectable with tissue to extend the existing spinal implant at least one vertebral level.

6. A spinal construct as recited in claim 1, wherein the second cavity extends through the first sidewall and the second sidewall, the cavities extending parallel to one another.

7. A spinal construct as recited in claim 1, wherein the body includes a second passageway that extends through the top wall and is in communication with the second cavity.

8. A spinal construct as recited in claim 1, wherein the first sidewall includes an inner surface that defines a groove, and further comprising a band that is expandable within the groove, the rod being engageable with the band to connect the rod with the body.

9. A spinal construct as recited in claim 8, wherein the band is expandable between a capture orientation and an expanded orientation.

10. A spinal construct as recited in claim 8, wherein the band is a circumferential ring that defines a gap.

11. A spinal construct as recited in claim 1, wherein the spinal construct includes an arm that is pivotable relative to the body about a pin that extends into the body to capture the existing spinal implant with the body.

12. A spinal construct as recited in claim 1, wherein the spinal construct comprises a bolt having a threaded shaft and a pair of arms configured to capture the existing spinal implant with the body, the threaded shaft being coupled to a nut to translate the bolt relative to the nut.

13. A spinal construct as recited in claim 12, wherein the arms axially translate relative to the body and pivot to capture the existing spinal implant with the body.

14. A spinal construct as recited in claim 1, wherein the body includes a hook shaped wall that defines the second cavity and captures the existing spinal implant with the body.

15. A spinal construct as recited in claim 1, wherein the hook shaped wall defines a side loading passageway to receive the existing spinal implant.

16. A spinal construct as recited in claim 1, wherein the rod defines an axis and includes a shaft that is offset from the axis.

17. A surgical system comprising:
   a rod;
   a spinal construct including a body having opposite first and second sidewalls and opposite first and second endwalls each extending from the first sidewall to the second sidewall, the body defining a first cavity and a second cavity configured for disposal of an existing spinal implant, the body including a circular opening in communication with the first cavity, a portion of the rod extending through the circular opening, the second sidewall being free of any openings in communication with the first cavity, an inner surface of the second sidewall engaging the portion of the rod to allow the rod to rotate relative to the body, the second cavity extending through the sidewalls, the body including a side loading passageway extending through the second sidewall and communicates with the second cavity, the body including opposite top and bottom walls each extending from the first sidewall to the second sidewall, the body including a coupling passageway extending through the top wall and in communication with the first cavity;

a coupling member through the coupling passageway and including between a first end surface and an opposite second end surface, the first end surface having a diameter greater than a diameter of the second end surface, the second end surface being concave and positioned within the first cavity to engage the portion of the rod; and an inserter engageable with the body to orient the passageway in alignment with the existing spinal implant for capture thereof.

18. A surgical system as recited in claim 17, further comprising a second coupling member engageable with the body and the existing spinal implant to fix position of the body relative to the existing spinal implant.

19. A surgical system as recited in claim 17, wherein the diameter of the first end surface is greater than a diameter of the coupling passageway.

20. A spinal construct comprising:

a rod;

a connector including an implant cavity configured for disposal of an existing spinal implant, the connector including opposite first and second sidewalls and opposite first and second endwalls each extending from the first sidewall to the second sidewall, the connector defining a rod cavity, the connector including a circular opening extending through the first sidewall, the circular opening being in communication with the rod cavity, the second sidewall being free of any openings in communication with the rod cavity, a head of the rod engaging an inner surface of the second sidewall, the head extending through the circular opening, the connector including opposite top and bottom planar walls each extending from the first sidewall to the second sidewall, a distance from the top wall to the bottom wall defining a maximum height of the connector, the connector including a passageway extending through the top wall and in communication with the rod cavity; and a coupling member extending through the passageway and including a first end surface and an opposite second end surface, the first end surface having a diameter greater than a diameter of the second end surface, the diameter of the first end surface being greater than a diameter of the passageway, the second end surface being concave and positioned within the rod cavity to engage and fix the rod in a selected orientation relative to the connector.

\* \* \* \* \*